US012806295B2

(12) United States Patent
Shukla et al.

(10) Patent No.: US 12,806,295 B2
(45) Date of Patent: Nov. 24, 2026

(54) MOLECULAR IMAGING COMPLEX FOR POSITRON EMISSION TOMOGRAPHY

(71) Applicants: Jaya Shukla, Chandigarh (IN); Rama Walia, Chandigarh (IN)

(72) Inventors: Jaya Shukla, Chandigarh (IN); Rama Walia, Chandigarh (IN)

( * ) Notice: Subject to any disclaimer, the term of this patent is extended or adjusted under 35 U.S.C. 154(b) by 642 days.

(21) Appl. No.: 18/260,246

(22) PCT Filed: Jan. 1, 2022

(86) PCT No.: PCT/IN2022/050001

§ 371 (c)(1),
(2) Date: Jul. 2, 2023

(87) PCT Pub. No.: WO2022/149159

PCT Pub. Date: Jul. 14, 2022

(65) Prior Publication Data

US 2024/0066157 A1 Feb. 29, 2024

(30) Foreign Application Priority Data

Jan. 5, 2021 (IN) ............................ 202111000313

(51) Int. Cl.
*A61K 51/08* (2006.01)
*A61K 38/095* (2019.01)
*C07B 59/00* (2006.01)

(52) U.S. Cl.
CPC ............ *A61K 51/08* (2013.01); *A61K 38/095* (2019.01); *C07B 59/008* (2013.01); *A61K 2123/00* (2013.01); *C07B 2200/05* (2013.01)

(58) Field of Classification Search
CPC .. A61K 51/08; A61K 38/095; A61K 2123/00; A61K 51/088; C07B 59/008; C07B 2200/05; A61B 6/037
See application file for complete search history.

(56) References Cited

FOREIGN PATENT DOCUMENTS

| | | |
|---|---|---|
| WO | 2009039981 A2 | 4/2009 |
| WO | 2019183625 A1 | 9/2019 |

OTHER PUBLICATIONS

Piotr Popik et al., "Long Term Facilitation of Social Recognition in Rats by Vasopressin Related Peptides: A Structure-Activity Study", Life Sciences, 1992, pp. 567-572, vol. 50, Issue 8.
Mirella Moro et al., "The Desmopressin Test in the Differential Diagnosis between Cushing's Disease and Pseudo-Cushing States", The Journal of Clinical Endocrinology & Metabolism, Oct. 1, 2000, pp. 3569-3574, vol. 85, Issue 10.
Thomas Ebenhan et al., "Peptide Synthesis, Characterization and 68Ga-Radiolabeling of NOTA-Conjugated Ubiquicidin Fragments for Prospective Infection Imaging with PET/CT", Nuclear Medicine and Biology, May 2014, pp. 390-400, vol. 41, Issue 5.
Anna Lucia Tornesello et al., "New Insights in the Design of Bioactive Peptides and Chelating Agents for Imaging and Therapy in Oncology", Molecules, Aug. 2, 2017, 22(8):1282.

*Primary Examiner* — Robert S Cabral

(74) *Attorney, Agent, or Firm* — Novel Patent Services LLC

(57) ABSTRACT

The present invention discloses complex for PET imaging in patients with Cushing's syndrome dependent on secretion of a hormone called ACTH from pituitary. This will help to distinguish Cushing's disease due to pituitary tumor (adenoma) or due to tumor of origin other than pituitary (ectopic Cushing's syndrome). It will also be helpful to delineate ACTH producing pituitary adenoma (corticotropinoma). More particularly the work disclosed an imaging complex comprising radiolabelled analogue of desmopressin for PET imaging to localize pituitary adenoma.

4 Claims, 5 Drawing Sheets

MOLECULAR IMAGING COMPLEX FOR POSITRON EMISSION TOMOGRAPHY

TECHNICAL FIELD

The present invention relates to an imaging complex for PET imaging in patients with Cushing's syndrome. More particularly the work provides an imaging complex comprising radioisotope, desmopressin analogue for imaging in adrenocorticotropin hormone (ACTH) dependent Cushing's syndrome. The invention particularly relates to delineating corticotropinoma and differential diagnosis of Cushing's syndrome i.e. to distinguish between Cushing's disease and ectopic Cushing's syndrome (ECS).

BACKGROUND ART

Cushing's syndrome (CS) occurs due to long-term exposure to inappropriately excessive production of cortisol from adrenal glands. On suspicion of the diagnosis, we need to biochemically confirm the presence of hypercortisolism. After confirmation of the hypercortisolism, the next step is to find out its ACTH dependency. ACTH levels above 20 pg/ml indicates that the hypercortisolism is ACTH dependent. For the management of ACTH dependent Cushing's syndrome it is required to distinguish Cushing's disease from ectopic Cushing's syndrome followed by anatomical as well as functional localization of the tumor in the sella. Anatomical imaging can delineate the tumor but cannot confirm its functionality, while vice versa is true for functional test/imaging.

Endogenous Cushing's syndrome is a disease resulting from inappropriate and endogenous superflous production of cortisol. This syndrome may arise due to excessive ACTH production from the pituitary gland, ectopic ACTH secretion from a non-pituitary source, autonomous cortisol secretion from adrenal glands and rarely by ectopic CRH production. The incidence of Cushing's syndrome is 1.2-2.4 cases/million/year and 70-80% are caused by Cushing's disease, of which 90% are due to microadenoma. Majority of the microadenoma are less than 6 mm in size. Visualizing these tumors in a 10 mm pituitary and confirming its functional status is a challenging task. In a patient with clinically and biochemically confirmed endogenous Cushing's syndrome the long term remission is determined by the correct functional and anatomical delineation of corticotropinoma i.e. to distinguish between Cushing's disease and ectopic ACTH production and preoperative visualization of the tumor. None of the available diagnostic modalities can localize and confirm the functionality of corticotropinoma simultaneously. In the differential diagnosis of Cushing's syndrome the most difficult distinction is between Cushing's disease and ectopic ACTH production. From a therapeutic point of view this distinction is essential so that patients with pituitary disease can be subjected to pituitary microsurgery, while patients with ectopic ACTH syndrome undergo resection of the primary tumor.

70 to 80% cases of ACTH dependent Cushing's syndrome are caused by Cushing's disease, of which 90% are due to microadenoma (<10 mm) majority being less than 6 mm. Visualizing these tumors in a 10 mm pituitary and confirming its functional status is challenging. In a patient with clinically and biochemically confirmed endogenous Cushing's syndrome the long term remission/cure is determined by the correct functional and anatomical delineation of the corticotropinoma i.e. to distinguish between Cushing's disease and ectopic ACTH production and preoperative visualization of the tumor, respectively. The treatment of choice in Cushing's disease is pituitary microsurgery, while ectopic ACTH syndrome require resection of the primary tumor. The current study aims to assess the utility of a novel integrated functional plus anatomical imaging modality in the differential diagnosis and localization of ACTH dependent Cushing's syndrome. if developed this modality will facilitate the management of the most enigmatic disorder in endocrinology.

None of the currently available diagnostic modality can achieve these goals simultaneously. Therefore, multiple tests are used to serve this purpose. The different tests used to localise the source of ACTH, include high dose dexamethasone test (HDDST), intravenous Corticotropin releasing hormone (CRH)/desmopressin stimulation, bilateral inferior petrosal sinus sampling (BIPSS) along with radiological (MRI, CT Scan) localisation (3). However, none of the tests alone is diagnostic. Pituitary tumor i.e corticotropinoma continues to express receptors for CRH and arginine vasopressin (AVP) as that of normal corticotrophs and rather, corticotropinomas are hyper responsive to these stimuli due to upregulation of the respective receptors.

Currently available test to distinguish pituitary microadenoma from ectopic Cushing's syndrome can be categorized as either functional or anatomical. The former includes high dose dexamethasone suppression test, CRH stimulation test, bilateral inferior petrosal sinus sampling (BIPSS) for ACTH gradient, while CEMRI sella is used for the latter purpose. The pretest probability of having a pituitary disease in ACTH dependent Cushing's disease is between 85 and 90%, which makes it mandatory that any additional test to have high specificity and hence necessitating multiple tests, all of which have their inherent limitations. (2) Importantly, BIPSS is an invasive test, use of which is further limited by its availability, need for high degree technical expertise and experience, high cost, and a false negative rate of 4%. Moreover, the positive predictive value for corticotropinoma lateralization is only 69%. Further, MRI is solely an anatomical imaging and cannot indicate the functional status of the tumor as evident by the presence of innocent pituitary incidentalomas in 10% of the population. (8) Thus, there is a need for a non-invasive integrated functional plus anatomical imaging for delineating corticotropinoma.

CRH and AVP are the major regulator of ACTH secretion from the anterior pituitary and act through their respective receptors. Though corticotropinoma are characterized by autonomous ACTH production, they retain their responsiveness to CRH and AVP as has been demonstrated by a rise in plasma ACTH and cortisol following intravenous administration of bovine CRH and as well as AVP. Desmopressin is a synthetic analogue of AVP. Desmopressin is more potent and specific for tumor corticotrophs and may be used for PET-CT imaging of ACTH Dependent Cushing's syndrome. A bifunctional chelator is required to radiolabel peptide, preserve the integrity and function of targeting molecule. Native Desmopressin does not have a conjugation site for DOTA, so we modified Desmopressin to conjugate with DOTA so that binding with corticotropinoma is not affected.

The present work discloses a novel integrated functional plus anatomical imaging modality using radiolabelled modified Desmopressin (mDesmo) or $^{68}$Ga-mDesmo PET/CT in the differential diagnosis and localization of ACTH dependent Cushing's syndrome. This a novel modality and has not been used previously. One study used $^{18}$F-Fluro-deoxy glucose (FDG)-PET/CT after intravenous administration of CRH (non-radioactive) and suggested that giving CRH prior to PET imaging improves the efficacy of $^{18}$F-FDG for detecting pituitary tumor. However, $^{18}F$-FDG is a nonspecific agent and the uptake of this is dependent on the metabolic activity of the tumor. It is taken up by all metabolic active tumors. Moreover, the interpretation of $^{18}F$-FDG PET/CT is difficult in pituitary as the brain parenchyma has a bright physiological uptake of $^{18}F$-FDG. $^{68}Ga$-mDesmo is taken up specifically by corticotropinoma and not by brain parenchyma and normal pituitary. Therefore, $^{68}Ga$-mDesmo PET/CT is a novel integrated functional plus anatomical imaging modality.

BRIEF DESCRIPTION OF FIGURES

The present invention will become more understandable from the description given herein and the accompanying drawings below. These are given by way of illustration only and therefore not limited to present invention and wherein.

BEST MODE(S) FOR CARRYING OUT THE INVENTION

Figure 1:
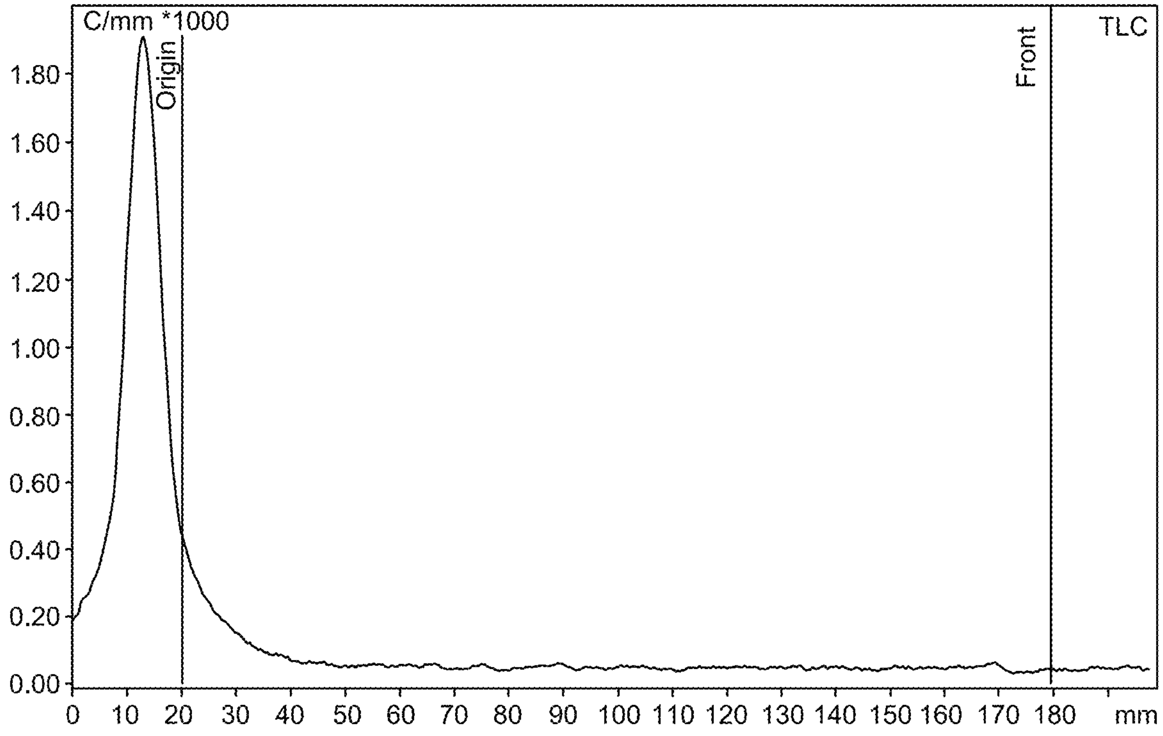
FIG. 1: Intensity v/s distance plot of $^{68}Ga$-mDesmo obtained with radio-TLC scanner using whatman paper 3 as a stationary phase and sodium citrate as mobile phase. Single peak of $^{68}Ga$-mDesmo with $R_f$ value 0.1, shows >99% radiochemical purity

The following presents a simplified description of the invention in order to provide a basic understanding of some aspects of the invention. This description is not an extensive overview of the present invention. It is not intended to identify the key/critical elements of the invention or to delineate the scope of the invention. Its sole purpose is to present some concept of the invention in a simplified form.

Accordingly, those of ordinary skill in the art will recognize that various changes and modifications of the embodiments described herein can be made without departing from the scope of the invention. In addition, descriptions of well-known functions and constructions are omitted for clarity and conciseness.

Features that are described and/or illustrated with respect to one embodiment may be used in the same way or in a similar way in one or more other embodiments and/or in combination with or instead of the features of the other embodiments.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It should be emphasized that the term "comprises/comprising" when used in this specification is taken to specify the presence of stated features, integers, steps or components but does not preclude the presence or addition of one or more other features, integers, steps, components or groups thereof.

The term "radiolabeling" disclosed herein refers to the binding of radionuclide with molecule of interest such as peptide.

The term "DOTA/NOTA/DOTAGA/NODAGA" disclosed herein refers to the organic compound used as a bifunctional chelating agent for positron emitting isotopes for PET imaging.

It should be emphasized that the term 'Desmopressin' disclosed herein refers to the 1-(3-mercaptopropanoic acid or Mpr)-Tyr-Phe-Gln-Asn-Cys-Pro-D Arg-Gly-NH2.

It should be emphasized that the term 'mDesmo disclosed herein refers to the complex of Desmopressin with bifunctional chelator DOTA.

It should be emphasized that the term '$^{68}Ga$-mDesmo disclosed herein refers to the radiolabelling of mDesmo with Ga-68 radioisotope.

It should be emphasized that the term "DOTA when used in this specification is taken to specify the 1,4,7,10-Tetraazacyclododecane-1,4,7,10-tetraacetic acid.

It should be emphasized that the term "DATA when used in this specification is taken to specify the ((6-pentanoic acid)-6-(amino)methy-1,4-diazepinetriacetate).

It should be emphasized that the term "NOTA" when used in this specification is taken to specify the 1,4,7-triazacyclononane-N,N',N"-triacetic acid It should be emphasized that the term "DOTAGA" when used in this specification is taken to specify the 2-[1,4,7,10-Tetraazacyclododecane-4,7,10-tris(t-butyl acetate)]-pentanedioic acid-it-butyl ester.

It should be emphasized that the term "NODAGA" when used in this specification is taken to specify the 2-[1,4,7-Triazacyclononan-1-yl-4,7-bis(tBu-ester)]-1,5-pentanedioic acid It should be emphasized that the term "PET (Positron Emitting Tomography)" disclosed herein refers to the nuclear medicine tomographic imaging technique using positrons.

It should be emphasized that the term "MRI" disclosed herein refers to the magnetic resonance imaging uses a strong magnetic field and radio waves to create detailed images of the organs and tissues within the body.

It should be emphasized that the term "radiological imaging" disclosed herein refers to the—imaging techniques such as X-ray radiography, ultrasound, computed tomography (CT), nuclear medicine including positron emission tomography (PET), and magnetic resonance imaging (MRI) are used to diagnose or treat diseases It should be emphasized that the term "corticotropinoma" disclosed herein refers to the pituitary adenoma made up predominantly of corticotrophs.

It should be emphasized that the term "bifunctional chelator" disclosed herein refers to the molecule that has ability to bind with biomolecule and has metal chelation property.

It should be emphasized that the term "differential diagnosis" disclosed herein refers to distinguish between Cushing's disease and ectopic Cushing's syndrome (ECS).

It should be emphasized that the term "Seq" disclosed herein refers to sequence of amino acids.

Embodiments

Desmopressin is a 9 amino acid long peptide bind to V2, V3 receptor. To develop a target specific ligand, it is of utmost importance to preserve the binding domain. The di-sulfide bridge between 2 cystein residue plays an important role in binding and stability of Desmopressin to the receptor.

Desmopressin has Seq-1(Mpr-Tyr-Phe-Gln-Asn-Cys(1)-Pro-D-Arg-Gly-NH2) with molecular weight −1069.

In an embodiment the Desmopressin analogue is prepared by adding/removing and/or modifying an amino acid at the N or/and C terminal of desmopressin.

In an embodiment the Desmopressin analogue comprising replacement of Mpr of Seq-1 with Cys, with Seq-2 (Cys-Tyr-Phe-Gln-Asn-Cys(1)-Pro-D-Arg-Gly-$NH_2$).

In an embodiment the Desmopressin analogue (Seq-3) involves the addition D-Phe at C terminal of Seq-2, with Seq-3 (D-Phe-Cys-Tyr-Phe-Gln-Asn-Cys(1)-Pro-D-Arg-Gly-NH2).

In an embodiment the Desmopressin analogue (Seq-4) involves the replacement of Gly-$NH_2$ with Thr(ol) at N terminal of Seq-3, with Seq-3 (D-Phe-Cys-Tyr-Phe-Gln-Asn-Cys(1)-Pro-D-Arg-Gly-$NH_2$).

In a preferred embodiment the Desmopressin analogue (mDesmo) is a 10 amino acid peptide with the sequence: (Seq-4: D-Phe-Cys-Tyr-Phe-Gln-Asn-Cys-Pro-Arg-Thr(ol) (disulfide cyclized Cys2-Cys7).

Conjugation of desmopressin analogue with bifunctional chelator (mDesmo): The desmopressin analogue (Seq-4) is of ten amino acid is conjugated with a bifunctional chelator.

In an embodiment the bifunctional chelator is conjugated to D-Phe.

In an embodiment the the bifunctional chelator is selected from the group comprising of DOTA, DATA, DOTAGA, NOTA, NOTAGA, NODAGA, Cyclic DTPA.

In an embodiment the molecular weight is mDesmo is 1648.89, when bifunctional chelator is DOTA.

Figure 2:
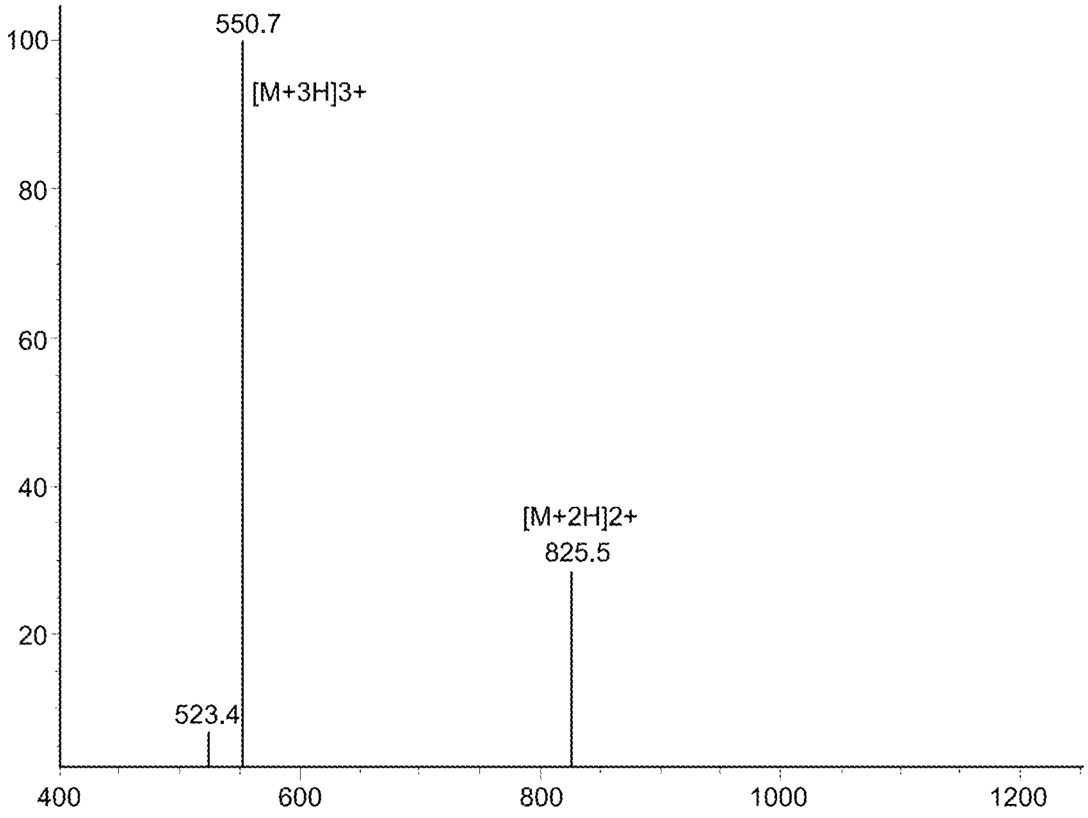
FIG. 2: MALDI-TOF of DOTA-D-Phe-Cys-Tyr-Phe-Gln-Asn-Cys-Pro-Arg-Thr(ol) (disulfide cyclized Cys2-Cys7) with molecular weight 1648.89.

In an embodiment FIG. 2 Illustrating MALDI-TOF of DOTA-D-Phe-Cys-Tyr-Phe-Gln-Asn-Cys-Pro-Arg-Thr(ol) (disulfide cyclized Cys2-Cys7) showing peak at 550.7 Da, 825.5 Da and a small peak at 523.4

Figure 3:
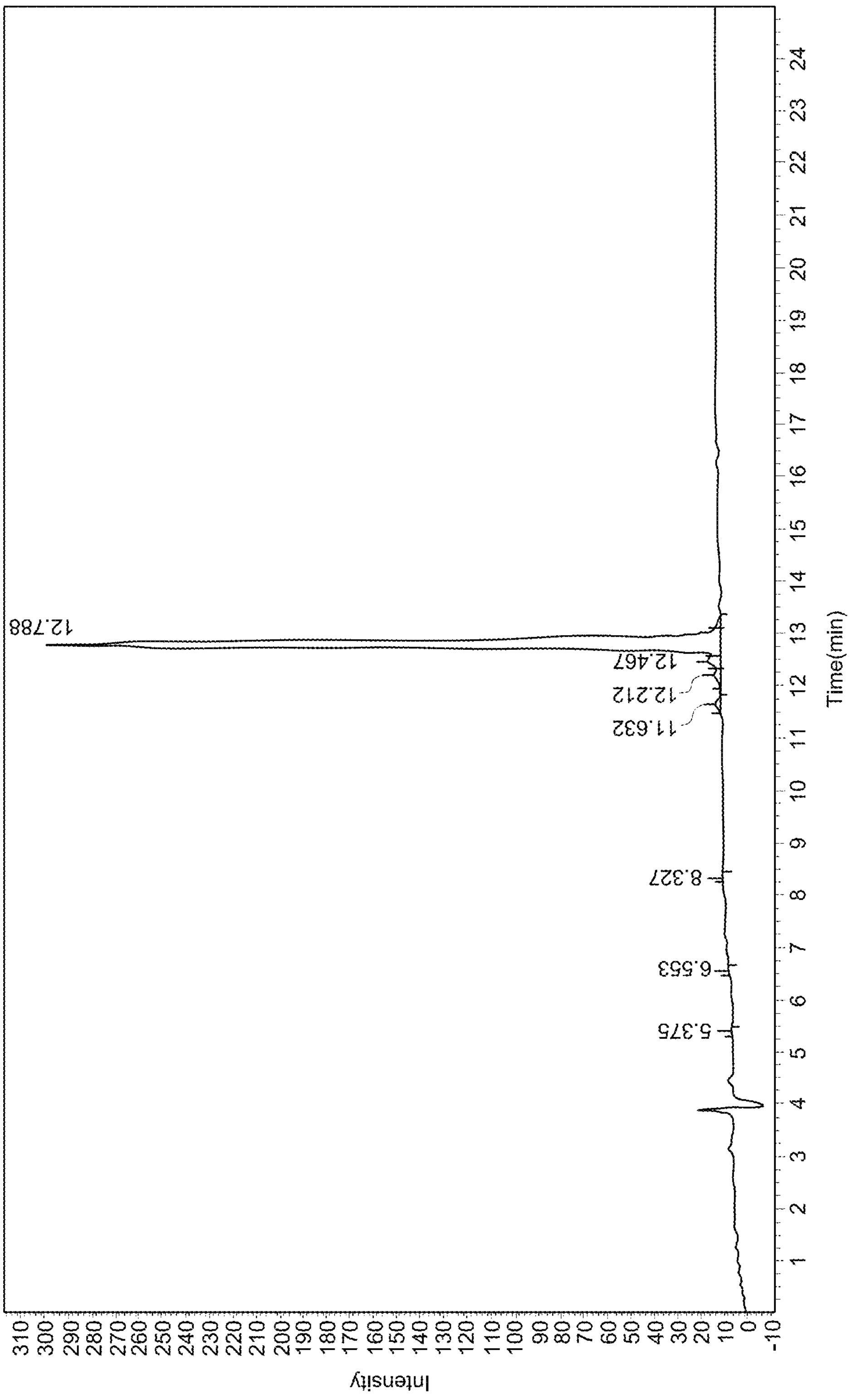
FIG. 3: HPLC of DOTA-D-Phe-Cys-Tyr-Phe-Gln-Asn-Cys-Pro-Arg-Thr(ol) (disulfide cyclized Cys2-Cys7)

In an embodiment FIG. 3 Illustrating HPLC of DOTA-D-Phe-Cys-Tyr-Phe-Gln-Asn-Cys-Pro-Arg-Thr(ol) (disulfide cyclized Cys2-Cys7) With retention time 12.77 minute.

Radiolabeling of mDesmo with $^{68}$Ga: For radiolabelling of mDesmo), $^{68}$Ga is eluted from $^{68}$Ge-$^{68}$Ga generator (iQS $^{68}$Ga Fluidic Labelling Module, itG, Germany). For standardization of radiolabeling parameters, various combinations of different reaction parameters such as pH (1-14), amount of peptide (1-100 μg), concentration and volume of sodium acetate buffer corresponding to $^{68}$Ga eluted with 4 mL of 0.05M HCl, incubation time (2-30 min) and temperature (25-100° C.) have been evaluated.

Purification: The residual free radionuclide ($^{68}$Ga) in the reaction mixture, if present, is subjected to removal as it gets accumulated in non-targeted organs thereby, altering the biodistribution, which ultimately leads to unnecessary radiation burden to the patient.

In an embodiment after radiolabeling, the reaction mixture is subjected to the purification using solid phase extraction (SPE) method with Sep-Pak C18 cartridges.

In an embodiment the C18 cartridge is first conditioned using 70% ethanol (5 mL) followed by washing with 10 mL water (HPLC grade) at the flow rate of 1-2 mL/min. The radiolabeled mixture is allowed to pass through cartridge enabling the hydrophobic interaction between the peptide and carbon chain of C18 cartridge. The trapped radiolabeled peptide is finally eluted with 1 mL of 50% ethanol with the flow rate of 1 m/min.

Radiochemical Purity: Radio thin-layer chromatography (radio-TLC) is performed to assess the radiochemical purity (RCP) of the in-house synthesized radiopharmaceutical ($^{68}$Ga-mDesmo). Various combinations of mobile phase solvents and stationary phases are assessed for their potential to demarcate the desired radiolabelled product ($^{68}$Ga-mDesmo) from free radionuclide ($^{68}$Ga) in the final reaction mixture. The $R_f$ values of $^{68}$Ga-mDesmo, and $^{68}$Ga are determined for each solvent and stationary phase using Radio-TLC scanner.

Stability: Shelf-life of $^{68}$Ga-mDesmo is assessed at room temperature up to 6 hours. Radio-chromatograms are obtained at various time points such as 30 min, 60 min, 120 min, 180 min, and 240 min using whatman paper 3 and sodium citrate as a stationary phase and mobile phase, respectively. In addition to that the stability of in house synthesized $^{68}$Ga-mDesmo is assessed in human serum at 37° C. for 4 hr.

In an embodiment the radiolabeling yield of >99% has been obtained when 5-25 mCi of $^{68}$Ga incubated with 1-100 μg of mDesmo at 70-100° C. for 2-30 min. The reaction pH is maintained at 1-14 using sodium acetate buffer and after incubation the crude reaction mixture is purified using C18 cartridge.

In a preferred embodiment the radiolabeling yield of >99% has been obtained when 25 mCi of $^{68}$Ga incubated with 20 μg of DOTA-DDAVP at 95° C. for 10 min. The reaction pH is maintained at 3.5-4.5 using 0.025 M sodium acetate buffer and after incubation the crude reaction mixture is purified using C18 cartridge. The product showed shelf life of 4 hr at room temperature, and was found stable in human serum stability up to 4 hr at 37° C.

In a embodiment the radioisotope is selected from the group consisting of Gallium-68, Indium-111, Yttrium-90, Lutitium-177, Zirconium-89, Copper-64.

Clinical Studies: The patients suspected with Cushing's syndrome are enrolled from the endocrine clinic of PGIMER, Chandigarh. The detailed patient history is taken, and physical examination is done. The complete hemogram and biochemistry are taken as baseline investigations. Hormonal evaluation includes serum cortisol obtained at 0800 h and 1100 h. Dexamethasone suppression test (LDDST): A dose of 0.5 mg dexamethasone is to be administered orally strictly every 6-hour interval for 48 h. Blood samples are collected for serum cortisol measurement at 0800 h on Day 3 following the first dose of dexamethasone. High dose dexamethasone suppression test (HDDST): Dexamethasone at a dose of 2 mg is to be administered orally strictly every 6 hours for 48 hours. Blood sample is collected for serum cortisol measurement at 0800 hr on Day 3 following the first dose of dexamethasone.

ACTH Induction Studies: Injection of 10 μg conjugated mDesmo intravenously is followed by estimation of ACTH and cortisol level after (15, 30, 45 and 60 min minutes to look for in-vivo efficiency of conjugated molecule to increase ACTH and cortisol levels.

PET/CT Imaging: An activity of 57 μCi/kg body weight of $^{68}$Ga-mDesmo (2-4 mCi) is administered intravenously in all patients. For three patients dynamic PET/CT imaging of brain is performed for 60 minutes with a dedicated PET/CT scanner (Discovery MIDR, GE Healthcare, USA) to observe maximum uptake time in the pituitary (sella) region. For rest of the patients, PET imaging will be performed for 10 minutes at optimum uptake time derived from dynamic studies to localize corticotropinoma. For all patients CT is acquired first followed by PET acquisition. The CT acquisition parameters used are tube voltage of 140 kVp, tube current (100-350 mA), 0.625 mm helical thickness, 0.8 s rotation time, and 0.531:1 pitch.

PET/CT processing protocol: The CT images were reconstructed in a matrix of 512×512 with a slice thickness of 0.625 mm. Data obtained from CT acquisition is used for attenuation correction of PET emission data and for fusion of attenuation corrected PET images with corresponding CT images. PET images were reconstructed in matrix of 384×384 using iterative reconstruction algorithm OSEM (32 subsets and 8 iterations). The reconstructed attenuation corrected PET images, CT images and fused images of matching pairs of PET and CT images are available for review in axial, coronal and sagittal planes, as well as in maximum intensity projections, three dimentional cine mode. A region of intrest (ROI) is carefully drawn around the site of the lesions. The slice with maximal uptake in the ROI is choosen for quantitative measurement of activity of the lesion (SUV). The SUV is calculated according to the formula described below.

SUV=Mean ROI activity(MBq/g)/Injected dose (MBq)/Body weight(g)

where, MBq=mega-Becquerel, and g=grams

Figure 4:
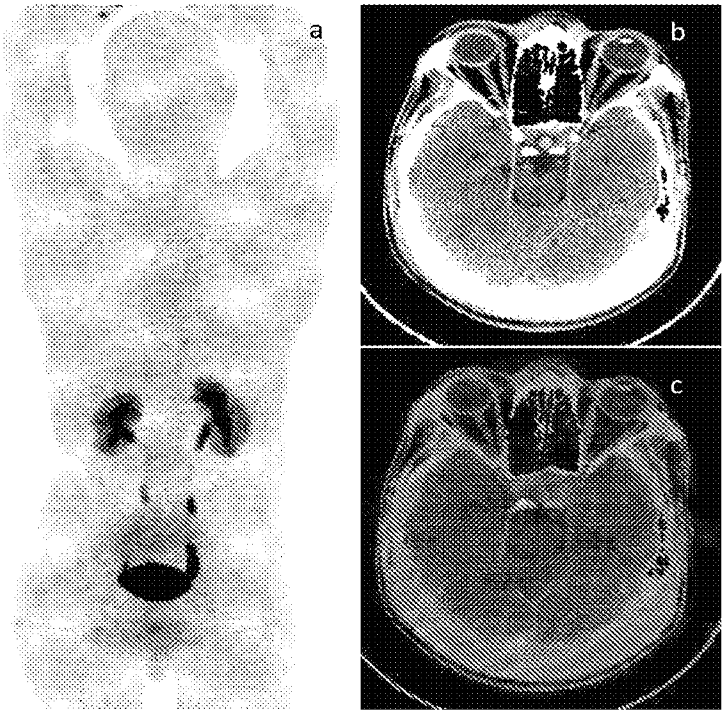
FIG. 4: a) MIP of Ga-68 mDesmo (radiotracer) PET showing no uptake in any organ throughout the body. Visualization of kidney and bladder demonstrating renal route of excretion of radiotracer, b) CT brain for anatomical details c) PET/CT fused image of brain and pituitary showing no radiotracer uptake.

As illustrated in FIG. 4. a) MIP of Ga-68 mDesmo (radiotracer) PET showing no uptake in any organ throughout the body. Visualization of kidney and bladder demonstrating renal route of excretion of radiotracer, b) CT brain for anatomical details c) PET/CT fused image of brain and pituitary showing no radiotracer uptake.

Figure 5:
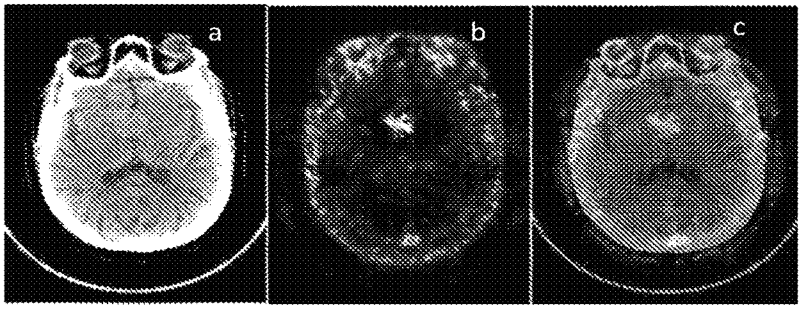
FIG. 5: A patient with macroadenoma on a) CT showing macroadenoma; b) PET and c) PET/CT fused images showing intense uptake (SUVmax 3.7) of radiotracer confirming specificity of radiotracer for pituitary adenoma.

As illustrated in FIG. 5. A patient with macroadenoma on a) CT showing macroadenoma; b) PET and c) PET/CT fused images showing intense uptake (SUVmax 3.7) of radiotracer confirming specificity of radiotracer for pituitary adenoma.

The processes above are described as a sequence of steps, this was done solely for the sake of illustration. Accordingly, it is contemplated that some steps may be added, some steps may be omitted, the order of the steps may be re-arranged, or some steps may be performed simultaneously.

Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

Many alterations and modifications of the present invention will no doubt become apparent to a person of ordinary skill in the art after having read the foregoing description. It is to be understood that the phraseology or terminology employed herein is for the purpose of description and not of limitation. It is to be understood that the description above contains many specifications; these should not be construed as limiting the scope of the invention but as merely providing illustrations of some of the personally preferred embodiments of this invention.

INDUSTRIAL APPLICABILITY

The invention particularly relates to differential diagnosis of Cushing's syndrome i. e. to distinguish between Cushing's disease and ectopic Cushing's syndrome (ECS). Cushing's syndrome is a clinical condition characterized by excessive circulating cortisol and by various clinical features such as gain of weight, menstrual, disturbances, hirsutism, psychiatric dysfunction, proximal muscle weakness, osteoporosis, fractures, loss of scalp hair, plethora, rounding of face, hypertension, easy bruising, wide purple striae, (>1 cm) hyper pigmentation, and diabetes. Cushing syndrome can be due to exogenous or endogenous causes.

Nevertheless, appropriate differentiation of Cushing's disease and ectopic Cushing's syndrome is a major challenge for physicians due to their non-specific clinical symptoms and variable results of biochemical tests. From a therapeutic point of view this distinction is essential so that patients can be assuredly referred for the treatment of choice.

Pituitary microsurgery is one of the major tools to cure the Cushing's disease, for this an accurate localization of the tumour and preserving normal pituitary functions are essential requirements. Nowadays, contrast enhanced Magnetic Resonance Imaging (MRI) has been used for imaging studies and this technique has a sensitivity of 70%. Moreover, sometimes MRI scanning also gives false positives results in patients suffering from pituitary incidentaloma. Bilateral inferior petrosal sinus sampling (BIPSS) is an invasive, technically demanding test with limited availability.

The present work discloses a novel integrated functional plus anatomical imaging modality using radiolabelled DOTA conjugated modified Desmopressin (mDesmo) or $^{68}$Ga-mDesmo PET/CT in the differential diagnosis and localization of ACTH dependent Cushing's syndrome. This is a novel modality and has not been used previously. One study used $^{18}$F-Fluro-deoxy glucose (FDG)-PET/CT after intravenous administration of CRH (non-radioactive) and suggested that giving CRH prior to PET imaging improves the efficacy of $^{18}$F-FDG for detecting pituitary tumor. However, $^{18}$F-FDG is a nonspecific agent and the uptake of this is dependent on the metabolic activity of the tumor. It is taken up by all metabolic active tumors. Moreover, the interpretation of $^{18}$F-FDG PET/CT is difficult in pituitary as the brain parenchyma has a bright physiological uptake of $^{18}$F-FDG. $^{68}$Ga-mDesmo is taken up specifically by corticotropinoma and not by brain parenchyma and normal pituitary. Therefore, $^{68}$Ga-mDesmo PET/CT is a novel integrated functional plus anatomical imaging modality.

We claim:

1. A molecular imaging complex, comprising:

a desmopressin analogue having an amino acid sequence D-Phe-Cys-Tyr-Phe-Gln-Asn-Cys-Pro-Arg-Gly-Thr (ol), wherein the peptide is disulfide cyclized between Cys2 and Cys7; and a bifunctional chelator conjugated to the D-Phe residue of the desmopressin analogue, wherein the bifunctional chelator is selected from the group consisting of DOTA, DATA, DOTAGA, NOTA, NOTAGA, NODAGA, and cyclic DTPA, and wherein the desmopressin analogue and the bifunctional chelator are present in a 1:1 molar ratio.

2. The molecular imaging complex as claimed in claim 1, is further conjugated with a radioisotope by heating the said complex with a radioisotope at 90-100° C. for 5-30 min at pH 3.5-4.5 using sodium acetate buffer, followed by purification using a C18 cartridge.

3. The molecular imaging complex as claimed in claim 2, wherein radioisotope is selected from the group consisting of Gallium-68, Indium-111, Yttrium-90, Lutitium-177, and Copper-64.

4. The molecular imaging complex as claimed in claim 1, wherein the molecular imaging complex is used for differential diagnosis and localization of ACTH dependent Cushing's syndrome.

* * * * *